United States Patent [19]

Brouillard

[11] 4,033,820
[45] July 5, 1977

[54] STARCH SPONGE COLUMN APPARATUS AND PROCESS FOR IMMOBILIZED ENZYME REACTIONS

[75] Inventor: Robert Ernest Brouillard, Cedar Rapids, Iowa

[73] Assignee: Penick & Ford, Limited, Cedar Rapids, Iowa

[22] Filed: Aug. 23, 1976

[21] Appl. No.: 716,518

[52] U.S. Cl. .................... 195/31 R; 195/31 F; 195/63; 195/68; 195/116; 195/139; 195/DIG. 11

[51] Int. Cl.² ............... C12D 13/02; C12B 1/00; C07G 7/02

[58] Field of Search ............ 195/63, 68, DIG. 11, 195/31 R, 31 F, 127, 139, 116

[56] References Cited

UNITED STATES PATENTS

| | | |
|---|---|---|
| 3,919,048 | 11/1975 | Dahlmans et al. .................. 195/63 |
| 3,944,470 | 3/1976 | Diehl et al. ......................... 195/63 |
| 3,960,663 | 6/1976 | Tamura et al. ..................... 195/31 F |

Primary Examiner—Lionel M. Shapiro
Attorney, Agent, or Firm—Tilton, Fallon, Lungmus, Chestnut & Hill

[57] ABSTRACT

A column apparatus and process is provided for immobilized enzyme reactions using a bed of starch in sponge form, the starch having been chemically modified to incorporate enzyme-immobilzing groups. The starch sponge bed of the column apparatus has a flow of direction length of 2 to 5 feet or more, and a water flow porosity such that over 0.5 (preferably over 1.0) gal.water/min.ft.² flows through the bed. The apparatus and process can be used with a wide variety of enzymes. It has applicability to the enzymatic conversion of starch hydrolysates, since the starch forming the sponge bed can be cross-linked to increase its resistance to enzyme attack. Starch-derived sugar syrups having D.E.'s of 40 to 97 can be produced. Also, isomerization of glucose syrups can be carried out to produce a syrup of enhanced sweetness, comprising a mixture of glucose and fructose.

14 Claims, 2 Drawing Figures

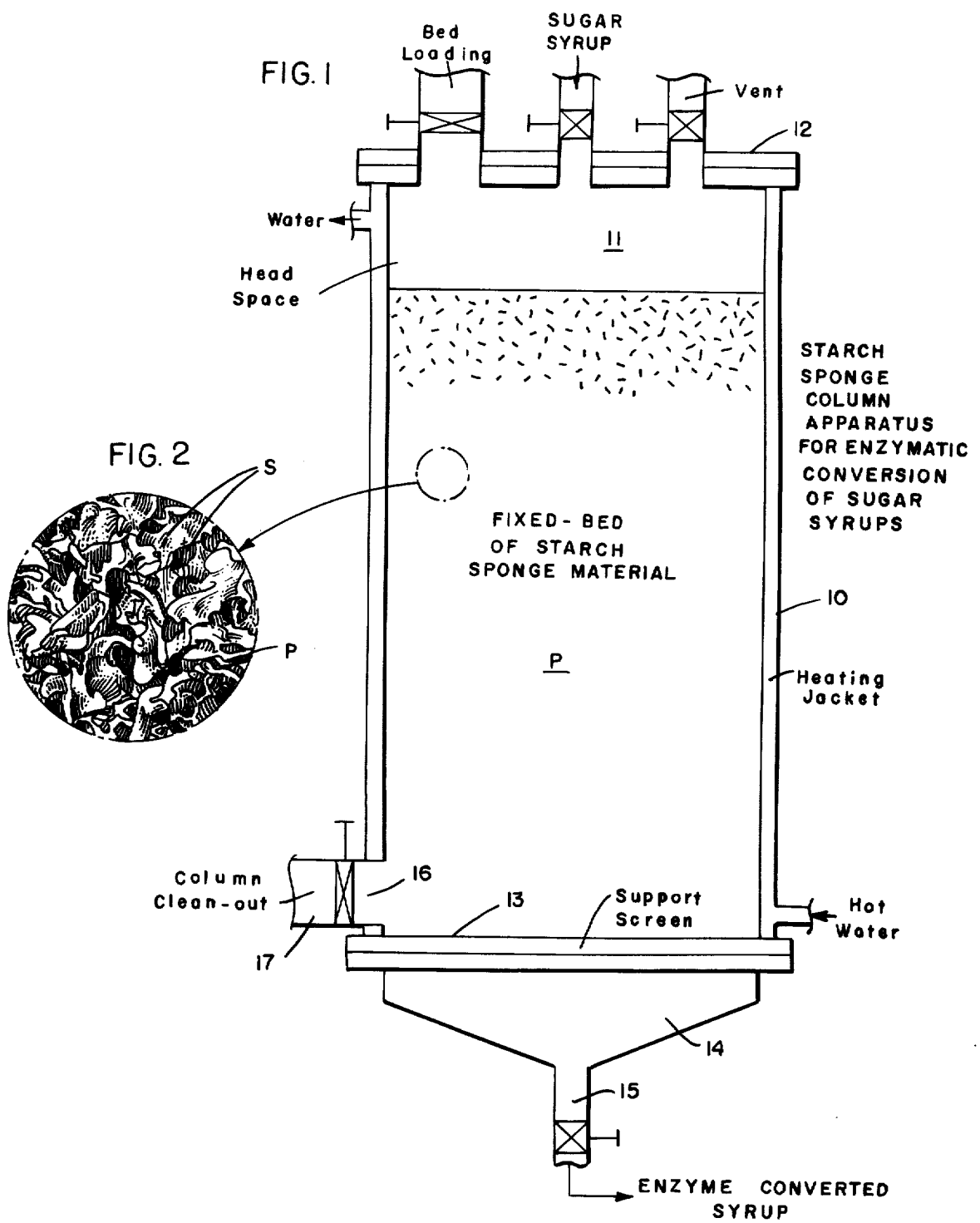

STARCH SPONGE COLUMN APPARATUS AND PROCESS FOR IMMOBILIZED ENZYME REACTIONS

BACKGROUND AND PRIOR ART

Enzymes have been recognized as biological catalysts since the early 1800's. They have achieved limited commercialization in industrial operations in the last fifty years.

A major deterrent to the large-scale industrial use of conventional water-soluble enzymes has been the high cost involved in one-time use. This obstacle has been removed by immobilization procedures which have resulted in water-soluble enzymes of great stability which can be used repeatedly. The life cycle of an immobilized enzyme is often twenty to forty times greater than experienced with the soluble form.

The earliest observation of enzyme immobilization was in 1916 (Nelson et al. J.A.C.S. 38, 1109 (1916)) deals with enzymes fixed on organic polymers and Mitz [Nature 189, 576 (1961)] covers covalent attachment to cellulose.

More recently, special emphasis has been on carbohydrates as the support for immobilized enzymes. Agarose [Gabel et al., J. Biochem 15, 410 (1970)], Dextran [Axen et al., Nature 210, 367 (1966)], Cellulose [Wheeler et al., Biochem, Biophys., Aeta 191, 187 (1969)], Collodian [Golden et al., Science 150, 758 (1965)], and various derivatized carbohydrates (Enzyme Tech., March 1973) as well as cellulosic fibers [Como et al., Die Starke 24, 420 (1972)] have been used.

The use of starch gels for immobilizing cholinesterase is known. For use in an analytical procedure Bauman et al., [Anal. Chem. 37, 1378 (1965)] combined the enzyme containing gel with a urethane foam, and used the composition in very thin layers with special precautions to avoid crushing the bed.

Goldstein et al [Biochem 9, 2323 (1970)] has described enzyme immobilization on a substrate prepared by the condensaton of dialdehyde starch with P, P'-diaminodiphenylmethane and subsequent reduction of the Schiff base followed by diazotization and reaction with the protein.

Immobilized enzymes have been used for analysis of various organic compounds including glucose, urea acetylcholine, and uric acid. Industrial utilization has involved DEAE-Sephadex L-amino acidacylase for the continuous resolution of DL-amino acids such as threonine and methionine.

A commercial application of enzymes immobilized on an ion exchange cellulose has been in connection with the partial conversion of starch-derived glucose to fructose, thereby obtaining a syrup of increased sweetness. For this purpose, glucose isomerase enzyme is bound to DEAE-cellulose (or similar cationic cellulose), and the glucose syrup is passed through a series of very thin beds of the isomerase-containing cellulose. See, Schnyder, B. J., "Continuous Isomerization of Glucose to Fructose on a Commercial Basis", Die Starke, 26, 409–412 (1974); and Thompson et al. U.S. Pat. No. 3,788,945, granted Jan. 29, 1974. This technology, as applied commercially by Standard Brands Incorporated and A. E. Staley & Company, involves the use of contact beds of 1 to 5 inches in thickness. This is necessary so that the pressure drop across each bed is small and the compaction of the bed is minimal. But because of the thinness of the beds, in order to avoid the effects of substrate channeling, it is essential to employ a series of such beds. Consequently, fixed-bed columns, such as are used for processes involving ion-exchange resins, cannot be employed. Instead, pressure leaf filters are used. The glucose isomerace bound to the cellulose carried is pumped as an aqueous slurry through the pressure leaf filter in such a manner as to cover each leaf evenly with a thin layer of the cellulose material. As disclosed in U.S. Pat. No. 3,788,945, the depth to width ratio of the beds is preferably limited to from about 0.02 to 0.05.

The plug flow column reactor is one in which the substrate is flowed through a fixed enzyme bed. For large-scale industrial operations, the plug flow reactor is preferred because it results in shorter cycles, lower equipment costs, and a generally more efficient operation. One of the major problems in the use of such reactors is resistance to flow through the immobilized enzyme bed. As the depth of the bed is increased, there is a great tendency for compaction of the bed due to the high pressures which must be employed to pass the substrate solution therethrough. When this occurs, the pressure drop across the bed will increase to such an extent that the pressure necessary to operate may be so high that conventionally constructed equipment cannot be used to contain the bed.

Because of the expense and inconvenience of carrying out glucose isomerization in pressure leaf filters, the corn syrup industry has been actively searching for alternative processes where the glucose isomerase enzyme can be immobilized on a material usable in commercial-size fixed bed columns, which operate as plug flow type reactors. Such column materials must effectively immobilize the enzyme; be chemically and physically stable, resisting disintegration under conditions of use; and being sufficiently porous while minimizing channeling effects, so that there is adequate and uniform contacting but with no excessive pressure drop across the bed. Some microorganisms which produce isomerase contain this enzyme in the cell, and the enzyme is bound therein, or can be bound by a heat treatment. For example, a column material can be prepared for Arthrobacter cells. One process is described in U.S. Pat. No. 3,821,086. Such natural column material shows considerable promise, and provides advantages over the use of shallow beds of cellulose-immobilized isomerase. However, the need is great for a column material of general utility, which can be used for immobilizing soluble isomerase, as well as other soluble enzymes, such as those used for the conversion of starch oligosaccharides to dextrose and maltose. Such a column material could be used to immobilize alpha amylase, glucoamylase, or mixtures thereof, for commercial production of corn starch-derived syrups having D.E.'s from 40 to 97.

In particular, to minimize capitol investment, increase plant capacity and reduce production costs, there has been a manifest need for a column process to produce intermediate D.E. corn syrups, such as the syrups now produced by enzymatic hydrolysis of corn starch to obtain syrups having a D.E. in the range of about 40 to 70. As far as is known, all present commercial processes for producing this type of syrup utilize a final stage batch enzyme treatment in which the soluble enzymes are dissolved in the syrup. This is a one-time enzyme use. Usually, the final stage involves treatment simultaneously with an alpha-amylase and a glucoamylase. Therefore it would be desirable to provide a column material to which a mixture of these enzymes can be chemically bonded and immobilized therein. Such a column material and column apparatus would also have many other applications, and could be used, in general, wherever batch enzyme treatments of substrates with soluble enzymes are now used.

SUMMARY OF INVENTION

The novel columnn apparatus and process for immobilized enzyme reactions of this invention is based in part on the discovery that an efficient and relatively inexpensive column material for immobilizing enzymes can be prepared from starch in sponge form. More specifically, the column apparatus for immobilized enzyme reactions of this invention includes column means providing a flow-through reaction chamber between the liquid inlet and outlet ends thereof, the reaction chamber extending for several feet in the direction of liquid flow. The improvement is characterized by providing a bed of starch in sponge form within the reaction chamber for liquid passage therethrough, the starch molecules of the sponge having been chemically modified to incorporate an effective amount of enzyme-immobilizing groups. The starch sponge bed has a flow direction length of at least two feet and preferably at least five feet, and a water flow porosity such that at least over 0.5 gallons and preferably over 1.0 gallons of water per minute per square foot of bed cross-section will flow therethrough without substantial liquid pressure drop due to the flow resistance of the starch sponge bed.

The enzyme immobilizing groups chemically bonded to the starch molecules are preferably cationic nitrogen groups, and the number of such groups based on added nitrogen can correspond from 0.2 to 5.0, and preferably 0.6 to 3.0 percent by weight nitrogen based on the dry weight of the unreacted starch. Where the apparatus or process involves the use of an enzyme capable of enzymatic attack on starch, the starch molecules may be cross-linked to increase the resistance of the starch sponge to enzyme attack. In this way, glucose, oligosaccharides derived from starch, and mixtures of glucose and oligosaccharides, may be treated with fungal or other alpha amylase, glucoamylase, and glucose isomerase, or mixtures of such enzymes, to produce a substrate of increased Dextrose Equivalent (D.E.) or increased sweetness by conversion of glucose to fructose.

THE DRAWING

The accompanying drawing in FIG. 1 illustrates a fixed-bed column apparatus utilizing a starch sponge bed in accordance with the present invention, the apparatus being illustrated in conjunction with the enzymatic conversion of syrups.

FIG. 2 is a greatly enlarged view of the material of the bed, which, in the illustration given, consists of small pieces of shreads of the starch sponge.

DETAILED DESCRIPTION

Starch in sponge form has been known for many years, but its practical uses have been very limited. Starch in sponge form can be readily prepared by heating an aqueous starch solution until a colloidal dispersion results, freezing this dispersion, and then thawing the frozen dispersion to obtain the porous starch sponge material. The starch sponge is insoluble in water at temperatures up to those which begin to gelatinize the starch. Literature references which illustrate the preparation of starch in sponge form include: S. Woodruff & L. R. Weber, J. Agric. Res., 1933, 46, 1099; and J. A. Radley, "Starch and Its Derivatives", D. Van Nostrand Co., Inc., page 63.

The starch sponge may be prepared in large sheets, pads, or blocks. While it may be used in this form for packing the column, it is preferably used in subdivided form, which facilitates the filling and uniform packing of a fixed-bed column. Exact sizing of the subdivided sponge material is not required. In general, the pieces of sponge material may range is size from 0.263 to 0.525 screen size (Tyler). It will usually be desirable to separate the ultra-fine material which may result from shredding or other breaking-up the sponge material for use in the column. In general, particles of sponge material having a screen size less than about 0.525 (Tyler) should be removed.

With starch sponge beds of the character described, there will be little or no pressure drop across the beds due to the flow resistance of the sponge material. Deep beds can therefore be employed. Even if a series of beds are used, the bed depths will be at least 2 feet in the direction of flow, and preferably at least 5 feet. The maximum bed depth or height, where the column extends vertically, can extend for as much as 40 to 50 feet, although typical columns may range from 5 to 20 feet in the direction of flow. The beds may be used in column apparatus having round, square, or rectilinear cross-sections. Usually the cross-sectional area will be substantially uniform throughout the length of the column. There is no limit on the lateral extent of the beds, although usually the diameter or lateral extents of the beds will range from about 5 to 15 feet. A typical column apparatus, therefore, might comprise a vertically-extending column, for either upfow or downflow contacting, having a height sufficient that a bed can be incorporated therein with some head room thereabove, having a height of from 8 to 20 feet, and a diameter of from 5 to 10 feet.

Columns prepared as described, will have a high degree of liquid porosity while avoiding channeling effects. More specifically, water can be flowed through beds of over 10 feet in height at flow rates in excess of 0.5 and preferably in excess of 1.0 gallon per minute per square foot of bed cross-sectional area. If the cross-section of the bed varies the smallest cross-section is used to determine flow rate. When an enzyme conversion is being conducted in the column, the rate of flow is only limited by the contact time necessary to achieve the desired conversion. There will be substantially no liquid pressure drop across the bed due to the flow resistance of the sponge material. For example, the solution to be contacted can be pumped into the top of a column having a head space above the fixed-bed of sponge material, at a rate maintaining a liquid level above the top of the bed. The outflow rate from the bottom of the bed can be controlled correspondingly, so that the liquid, in effect, percolates through the bed without any pump pressure being required. The difference in static head between the top and the bottom of the bed, will be due to the height of the liquid in the column, and not to the resistance of the sponge bed. Alternatively, the solution to be contacted can be pumped into the bottom of the column flowing upwardly through the bed, the head space above the bed being maintained substantially full of the contacted liquid. The outflow will be controlled in relation to the inflow, and the pump pressure required for the operation being only that necessary to move the liquid against its own static head, and not due to the resistance of the sponge material itself. As will be understood, the beds can also be used so that the flow direction is horizontal, although more commonly, the beds will be used in vertically-extending columns with a downwardly direction of flow.

For the purpose of the present invention, the starch used to form the sponge material is chemically modified to incorporate an effective amount of enzyme-immobilizing groups. In general, reagents bonding immobilizing groups to the starch chains through ether linkages can be employed. Cationic groups are preferred but enzyme-immobilizing anionic groups are also known, and could be used for some purposes. A wide variety of cationic etherifying agents can be employed, such as those described in U.S. Pat. Nos. 3,823,133 and 3,809,605 for cellulose. Further, where required to chemically stabilize the starch cross-linking procedures can be used. Suitable procedures for this purpose are described in the literature, for example, in Guthrie et al, *Ind. J Engr. Chem.*, 52, 915–917 (1960) with reference to cellulose. As is known in the art, tertiary amine and quaternary ammonium groups are particularly effective for immobilizing enzymes. The starch before conversion to sponge form may therefore be modified to incorporate the di- and tri-ethylaminoethyl groups, providing DEAE-starch or TEAE-starch respectively. Alternatively, the starch can be reacted according to known procedure with epichlorohydrin and triethanolamine to form ECTEOLA-starch, which is then formed into a sponge.

In general, where cationic nitrogen groups are introduced as the immobilizing groups, the number of such groups on the basis of added nitrogen can correspond to from 0.2 to 5.0 percent by weight nitrogen based on the dry weight of the unreacted starch. Capacity increases with the nitrogen. Sufficient capacity is usually obtained where the cationic nitrogen groups, such as tertiary amine groups or quaternary ammonium groups, are present in an amount corresponding to the range of from 0.6 to 3.0 percent added nitrogen. For some purposes, a useable substitution level can be as low as 0.2 to 0.5%, on the same basis.

The column apparatus and column process of this invention for immobilized enzyme reactions is applicable to all enzymes which are immobilized by the functional groups, and which do not attack or degrade the structure of the sponge. In general, enzymes as a class are adsorbed and immobilized by cationic nitrogen groups, such as tertiary amine or quaternary ammonium groups. Cross-linking of the strach can increase its resistance to attack by starch converting enzymes.

When certain enzymes are used, it is advantageous to cross-link the starch to prevent degradation of the sponge structure during use. This is particularly so when enzymes of the hydrolase group such as amyloglucosidase are used. Among the suitable cross-linking agents are formaldehyde, glyoxal, glutaraldehyde, and phosphorous oxychloride and various synthetic resins such as urea formaldehyde or melamine formaldehyde.

One suitable procedure involves cross-linking a preformed starch sponge, and then derivatizing to achieve an enzyme absorbing product. By cross-linking first, the structure of the sponge is protected during derivatizing. The level of cross-linking can be from 25 to 100 percent by weight based on the dry weight of the unreacted starch.

For enzymatic conversion of glucose, and mixtures of glucose with oligosaccharides derived from natural starch, such as corn starch, the enzymes will be those which have heretofore been employed for such purposes, particularly fungal or other alpha-amylase, glucoamylase or mixtures of alpha amylase and glucoamylase. For conversions of glucose syrups to mixtures of glucose and fructose, glucose isomerase can be employed. For this purpose, a high D.E. feed stock is preferred, such as a starch derived glucose solution having a D.E. of 93 to 97, indicating that it is composed of large amounts of dextrose. For producing intermediate D.E. syrups from corn starch or other starch materials, the feed stock can be a starch derived mixture of glucose and oligosaccharides having a D.E. in the range of 15 to 45. For example, a mixture of alpha-amylase and glucoamylase enzymes can be applied to a cross-linked, derivatized starch sponge material, and employed with a feed stock of the character described to produce products having D.E.'s in the range of 42 to 70. These are important commercial products which are now produced entirely by batch-type enzyme conversions involving one-time use of the enzymes. With the process of the present invention, the useful life of the enzymes may be greatly extended, being usable for converting at least 10 to 20 times the amount of substrate to the intermediate D.E. corn syrup of commerce.

Other enzymes which can be used in the process and apparatus of this invention include trypsin, papain, chymotrypsin, lactase, urease, acylase, catalase, penicillin-amidase, betaamylase, lipase, glucose oxidase, protease, gelatinase, hemicellulase, pectinase, lysozyme, pepsin, etc.

The apparatus and process of this invention are further illustrated by the following examples.

EXPERIMENTAL EXAMPLES

Example 1

Potato starch was slurried in water to a concentration of 22 Be. and a salt-caustic solution containing saturated sodium chloride and 30% sodium hydroxide was added under non-gelatinizing conditions to yield 10% salt based on the weight of the water and 2.6% caustic based on the starch. An amount of 3-chloro-2-hydroxypropyl trimethylammonium chloride equal to 7% of the weight of the starch was added and the mixture reacted at 115° F. for 24 hours. Thereafter, the slurry was adjusted to pH 1 with hydrochloric acid. Heating was continued until the starch derivative had been acid modified to a 5 gram Alkali Fluidity of 17 ml. (Chemistry and Industry of Starch, 2nd Ed., R. W. Kerr, Academic Press, N.Y., 1950, p. 133.) Thereafter, the starch slurry was adjusted to pH 4, with soda ash. The product was filtered and washed by resuspending in water twice, filtering, and recovering the product each time. The final starch product was air dried. An analysis indicated that the cationic starch product contained 0.35% added nitrogen. When stained with Fast Green S F dye solution, the granules became green, indicating strong cationic activity.

A cationic starch sponge was prepared from the described product using the following procedure: Three gallons of a suspension containing 8% by weight of cationic starch in water was cooked at 195° F. for 15 minutes. After cooling to room temperature, the entire quantity in a three-gallon container was placed in a quick freeze unit at 0° F. and kept at this temperature for 72 hours. Afterward, the frozen cationic starch was removed and placed in room temperature for an additional 72 hours. At the end of this period, the starch sponge was placed in a wine press and excess water removed such that the wet sponge contained from 64 to 75% moisture.

Example 2

A quantity of 769 grams of cationic starch sponge containing 200 grams dry substance material was suspended in 400 ml. of water and adjusted to pH 10–11 with calcium hydroxide. While maintaining the pH at 10–11, and amount of 60 grams of phosphorous oxychloride was added dropwise with stirring over a period of about 2 hours. Finally, the pH was adjusted to 4 with hydrochloric acid and the product washed with four volumes of water on the filter. A portion of the final product was then placed in an oven at 50° C. until dry, and another undried portion was further treated with enzyme and resin in the following manner: One hundred forty-eight grams of damp starch sponge (50 grams dry basis) was mixed in a Hobart Blender with 50 ml. of glucoamylase solution (Diazyme L-100, Miles Chemical Co., Elkhart, Indiana), along with 25.0 grams of Tybon 8003 (Pacific Resins and Chemicals, Tacoma, Washington) in 25 ml. of water. The pH of the mixture was adjusted to 4.2. After stirring to insure uniform mixing, the mixture was placed in an air dryer at about 50° C. for 48 hours. Thereafter, the product was placed on a 20-mesh screen to remove any fines and the product thus prepared was ready for use in a column for the preparation of syrups.

Example 3

Stabilized (cross-linked) starch sponge containing bonded glucoamylase as prepared in Example 2 was placed in a 1-inch diameter column, and 25% solids concentration syrup at 20% D.E. (dextrose equivalent; Standard Analytical Methods, Corn Refiners Association, Method E-26) flowed through the column at a rate of 1.1 ml./minute at pH 4.2 and 140°F. The D.E. of the effluent syrup was 84.9%. After five days of operation, the column was shut down while still producing 85.7% D.E. syrup.

Example 4

Cross-linked starch sponge as prepared in Example 2 was stabilized and treated with resin and enzyme in preparation for column operation.

Eight hundred grams of starch sponge at 75% moisture content (200 grams d.b.) was slurried in tap water and the pH adjusted to 10–11 with calcium hydroxide. Phosphorous oxychloride in an amount of 80 grams was added over a period of two hours while maintaining pH 10–11. The product was then adjusted to pH 4.2, dewatered on a filter, and washed twice with ion exchanged water. Wet sponge was then contacted with 250 ml. of Diazyme L-100 enzyme solution (27% solids), 150 grams of Tybon 8003 (56% on d.s. starch sponge), and 100 grams of water. The mixture was adjusted to pH 4.2 and dried at 50° C. for 48 hours. Fines were separated on a 20-mesh screen, yielding 353 grams retained on the screen.

An amount of 190 grams of dried enzyme bonded starch sponge was soaked in pH 4.0 buffer solution for a few minutes before placing in a 1-inch diameter column. Carbon refined feed syrup at 20% D.E., pH 4.2, 25% solids concentration, and 140° F. was flowed into the top of the column. The flow rate was varied from 1.5 ml./min. to 3.4 ml./min. The D.E. of the effluent syrup ranged rom 94.6% at 2.2 ml./min. to 88.0% at 3.4 ml./minute.

During operation of the column, the feed syrup was changed to ion exchanged syrup at 42% D.E. The solids was adjusted to 26.8% concentration; other parameters being the same. When the flow of syrup through the column was varied from 2.2 ml./min. to 15.0 ml./min., the D.E. of effluent syrup ranged from 92.9% to 78.1% respectively.

Prior to terminating the column, it was determined that 28,453 grams dry substance of 20% D.E. syrup and 6,290 grams dry substance of 42% D.E. syrup had been passed through the column.

OTHER EXAMPLES

Example 5

The procedures described in Examples 1, 2, and 3 can be repeated using diethyl-amino-ethyl chloride, triethyl aminoethyl chloride, or cyanogen bromide. Substantially similar results will be obtained.

Example 6

The procedure of Example 2 can be repeated using invertase or glucose oxidase, or glucose isomerase, or catalase or urease. For all of these enzymes, the starch sponge will absorb the enzyme from an aqueous solution, and can be used for column operation.

Example 7

A starch sponge carbonate can be prepared from ethyl chloroformate, as described in Example 1 of U.S. Pat. No. 3,810,821 and the teachings of Example 1 of this application. It will absorb amyloglucosidase from a water solution so that it cannot be removed by water washing. The enzyme containing sponge when put in a down-flow column can be used to obtain D.E.'s ranging from 60 to over 90, using a corn syrup substrate with a D.E. of 34. No back pressure problems will be encountered unless the sponge material is in too fine a state of subdivision.

Example 8

A carboxymethychloro-S-triazinyl derivative of a starch sponge can be prepared according to Example 1 of U.S. Pat. No. 3,278,392 and the teachings of Example 1 of this patent application which will absorb urease from an aqueous solution. The enzyme can be firmly bound so that it cannot be removed by water washing. When the enzyme containing sponge is put in a column and a urea solution is down-flowed, the effluent will contain substantially no urea. After extended use, the column should still be effective, and should show no significant back pressure.

COMMERCIAL EXAMPLES

The following examples are intended to illustrate preferred commercial practice, as presently envisioned.

Example 9

A column apparatus is employed of the kind conventionally used with ion exchange resins. Such an apparatus is illustrated diagrammatically in FIG. 1. The vertically-extending column 10 provides internally a space for receiving the fixed-bed of starch sponge packing P. Above the material there is provided an open head space 11. The column 10 is provided with a heating jacket, as indicated in FIG. 1, through which hot water can be circulated for maintaining a selected temperature during the enzyme reaction. The top or cover of the column 12, which may be removable, is provided with a series of connections, the larger one on the left, as indicated, being used for loading the starch sponge material into the bed, the center one for supplying the solution to be converted, such as a starch hydrolysate sugar syrup, and the one on the right to be used as an air vent. All of these inlets may be provided with suitable valves, as shown. The bottom of the bed is supported on a screen 13, which retains the sponge material of the bed, while permitting liquid flow therethrough into the tapered bottom portion 14 which converges to outlet 15. The outflow through 15 is controlled by means of a valve, as indicated. Immediately above screen 13 on one side of the column, there is provided a clean-out opening 16 which communicates with a removal pipe 17 through a valve, as shown. With this arrangement when the starch sponge material is in sub-divided condition, it can be pumped into the column in the form of a water slurry, the bed loading inlet at the top being used. After repeated use of the sponge bed, it may be desirable to remove the bed material, and replace it with a new starch sponge bed. This can be done by introducing water through the bed loading and/or syrup inlets at the top, the valve being opened on outlet pipe 17, and the bed material being pumped out as slurry through pipe 17.

The form of the column material is illustrated in FIG. 2. It consists of pieces or shreds S of varying size. Preferably, the particle size is in the range of 0.263 to 0.525 screen size (Tyler).

In the use of the apparatus of FIG. 1, such as for conversion of a syrup with an appropriate enzyme, the syrup is pumped into the head space 11 at the top of the column, and a level is maintained therein above the top of the bed of cellulose sponge material, as indicated at 18. The valve on outlet line 15 is opened to permit outflow at substantially the same rate as the inflow, the column 10 being maintained full of the aqueous syrup to be converted. In this operation, the syrup flows downwardly through the bed at a rate, which is sufficient to achieve the level of conversion desired. The height and diameter of the bed may be varied, as required, for the particular process. In the processes described in the following examples, the bed of starch sponge material, for example may have a height of about 12 feet and a diameter of about 8 feet.

Example 10

Starch sponge is prepared by cooking a 10-25 Alkali Fluidity starch at 8% solids concentration in water at 195° F. for 15 minutes. The starch slurry is cooled to room temperature and placed in five-gallon containers for quick freezing at 0° F. After about 72 hours, the containers are removed to room temperature and the mixture allowed to thaw. Thereafter, the sponge is placed in a hydraulic press and the water content lowered to about 60 to 75%. The sponge may be kept under refrigeration in this condition.

Damp starch sponge (30 pounds) is suspended in 60 pounds of water containing 30 pounds of sodium chloride and calcium hydroxide at pH 10-11. A quantity of 30 pounds of phosphorous oxychloride is added over a period of about two hours. During this time, the mixture is agitated slowly in a jacketed stainless steel ribbon blender and the pH is maintained at 10-11 by addition of calcium hydroxide as required.

The mixture is then treated with 17 pounds of calcium hydroxide and 4.5 pounds of diethylaminoethyl chloride hydrochloride. Agitation is continued for the 1.5-hour reaction time while maintaining the temperature of reaction at 50° C. At the end of this period, the reaction mixture is adjusted to pH 4 with hydrochloric acid filtered and washed by resuspending twice, recovering the product each time and at the end. The final product is air dried to equilibrium moisture and may be expected to contain about 1% added nitrogen.

Stabilized cross-linked cationic starch sponge is placed in stainless steel column 3 feet × 12 feet to a height of about 6 feet using approximately 150 pounds of starch sponge. Water is added to swell the sponge in the column and an amount of cell-free enzyme from Streptomyces (ATCC 21175) prepared as in Example 1 of U.S. Pat. No. 3,788,945 is circulated through the column. A substrate syrup at 95% D.E. and pH 8.0 is passed through the column at commercially acceptable flow rates to yield a product with 42% fructose, about 50% dextrose, and the remainder higher saccharides.

Example 11

Example 10 is repeated using a mixture of enzymes for attachment to the cationic starch sponge. A solution containing about 20 pounds of Fungamyl (Novo Enzyme Corp., Mamaronek, N.Y.) in water is circulated through the column for 2 hours, followed by circulation of a solution of about 10 pounds of G-zyme (Enzyme Development Co., N.Y., N.Y.) for another 2 hours.

A starch syrup hydrolyzate ranging from 20 to 42% D.E. may then be passed through the column at 125°130° F. to yield a syrup in the range of 60-67% D.E. at a pH of 5.5 to 6.0 containing a dextrose:maltose ratio of about 1:1.

Example 12

Example 10 is repeated using only a glucoamylase (G-zyme) for attachment to the sponge. The enzyme is added in the manner of Example 11, and the column operating conditions are adjusted to convert a 15-25% D.E. syrup at pH 4.0-4.5 at a temperature of 140° F. to an effluent syrup of about 95% D.E.

Example 13

To prevent bacterial contamination from rendering the column ineffective, the column containing cationic sponge may be treated from time to time with bacterial agents. For example, the column can be sweetened off (diluted out with water), and an aqueous solution of a bactericide flushed into the column at normal operating temperature. After a suitable residence time, the column is then sweetened on (substrate syrup added) and normal column operation resumed.

Representative reagents usable as bactericides and the conditions of their use are as follows:

Formaldehyde is added in a ratio of 1 gallon of 37% reagent for each 100 gallons of volume. After 3 to 24 hours, the column is rinsed for at least 2 hours with water before adding syrup again.

Chlorine as chloromelamine may be added to the column to yield about 10 ppm concentration using about 6 grams per cubic foot of reagent. The chlorine is allowed contact with the sponge for 1-2 hours and is thereafter flushed with water before sweetening on with syrup. Additional enzyme may be added as needed.

Sulfur dioxide in an amount of 0.5 to 1.0% may also be used to remove bacteria from the column. Similar washing and sweetening on procedures are suitable.

Quaternary ammonium products in mixtures such as alkyl dimethyl benzyl ammonium chloride and dehydroabietylamine may be used in concentrations up to 20% of the weight of the sponge and may be incorporated directly with the sponge after formation of the cationic sponge. Subsequent refining techniques remove all traces of bactericide.

I claim:

1. Column apparatus for immobilized enzyme reactions, including column means providing a flow-through reaction chamber between the liquid inlet and outlet ends thereof, said reaction chamber extending for several feet in the direction of liquid flow, wherein the improvement comprises: a bed of starch in sponge form provided in said reaction chamber for liquid passage therethrough, the starch molecules of said sponge having been chemically modified to incorporate an effective amount of enzyme-immobilizing groups, said starch sponge bed being characterized by having a flow direction length of at least 2 feet and a water flow porosity such that over 0.5 gallons of water per minute per square foot of bed cross-section will flow therethrough without substantial liquid pressure drop due to flow resistance of the starch sponge bed.

2. The improved column apparatus of claim 1 wherein said reaction chamber and said starch sponge bed have a flow direction length of at least 5 feet.

3. The improved column apparatus of claim 1 wherein said starch sponge bed has a water flow porosity such that more than 1.0 gallon of water per minute per square foot of bed cross-section will flow therethrough without substantial liquid pressure drop across the length of the bed due to the flow resistance of the sponge bed.

4. The improved column apparatus of claim 1 in which the enzyme-immobilizing groups chemically bonded to said starch molecules are cationic nitrogen groups, the number of said groups on the basis of added nitrogen corresponding to 0.2 to 5.0 percent by weight nigrogen based on the dry weight of the unreacted starch.

5. Column apparatus for immobilized enzyme reactions, including column means providing a flow-through reaction chamber between the liquid inlet and outlet ends thereof, said reaction chamber extending for several feet in the direction of liquid flow, wherein the improvement comprises: a bed of starch in sponge form provided in said reaction chamber for liquid passage therethrough, the starch molecules of said sponge being chemically bonded to cationic nitrogen groups effective for enzyme-immobilization, said groups being selected from tertiary amine groups and quaternary ammonium groups, said groups being present in an amount corresponding to 0.6 to 3.0 percent added nitrogen based on the dry weight of the starch, said starch sponge bed having a flow direction length of at least 5 feet, and a water flow porosity such that more than 1.0 gallon of water per minute per square foot of bed cross-section will flow therethrough without substantial liquid pressure drop across the length of the bed due to the flow resistance of th sponge bed.

6. The process for reacting a water-soluble enzyme-convertible substance with an enzyme in which a water solution of the substance is passed through a porous bed of material containing immobilized therein at least one enzyme for the reaction, wherein the improvement comprises employing as said bed starch in sponge form which has been chemically modified to incorporate an effective amount of enzyme-immobilizing groups, said starch sponge bed having a flow direction length of at least 2 feet, and passing said water solution through said bed at a rate of over 0.5 gallon of solution per minute per square foot of bed cross-section.

7. The process of claim 6 in which said bed of sponge material has a flow direction length of at least 5 feet.

8. The process of claim 6 in which said solution is passed through said bed at a rate of more than 1.0 gallon of solution per minute per cubic foot of bed volume.

9. The process of claim 6 in which the enzyme-immobilizing groups chemically bonded to said starch are cationic nitrogen groups, the number of said groups on the basis of added nitrogen corresponding to 0.2 to 5.0 percent by weight nitrogen based on the dry weight of the strach.

10. The process for reacting a water-soluble enzyme-convertible substance with an enzyme in which a water solution of the substance is passed thorugh a porous bed of material containing immobilized therein at least one enzyme for the reaction, wherein the improvement comprises employing as said bed starch in sponge form, the molecules of said starch having been chemically modified to incorporate an effective amount of enzyme-immobilizing cationic nitrogen groups, said groups being selected for tertiary amine groups and quaternary ammonium groups and being present in an amount corresponding to 0.2 to 5.0 percent added nitrogen based on the dry weight of the starch, said starch sponge bed having a flow direction length of at least five feet, and passing said solution through said bed at a rate of over 1.0 gallon of solution per minute per square foot of bed cross-section.

11. The process of claim 10 in which said starch molecules are cross-linked to increase the resistance of said starch to enzyme degradation.

12. The process of enzymatically converting a sugar substrate selected from the group consisting of glucose, oligosaccharides derived from starch, and mixtures of glucose and said oligosaccharides, in which a water solution of said sugar substrate is passed through a porous bed of material containing immobilized therein at least one enzyme for said conversion selected from the group consisting of alpha amylase, glucoamylase, and glucose isomerase, wherein the improvement comprises employing as said bed starch in sponge form, the molecules of said starch having been cross-linked and chemically modified to incorporate an effective amount of enzyme-immobilizing groups therein, said starch sponge bed having a flow direction length of at least five feet, and passing said sugar solution through said bed at a rate of over 1.0 gallon of solution per minute per square foot of bed cross-section.

13. The process of claim 12 in which the enzyme-immobilizing groups chemically bonded to said starch are cationic nitrogen groups, the number of said groups on the basis of added nitrogen corresponding to 0.2 to 5.0 percent by weight nitrogen based on the dry weight of the unreacted starch.

14. The process of claim 12 in which said enzyme-immobilizing groups chemically bonded to said starch are cationic nitrogen groups selected from tertiary amine groups and quaternary ammonium groups, said groups being present in an amount corresponding to 0.6 to 3.0 percent added nitrogen based on the dry weight of the unreacted starch.

* * * * *